(12) United States Patent
Goble

(10) Patent No.: US 6,325,799 B1
(45) Date of Patent: Dec. 4, 2001

(54) ELECTROSURGICAL INSTRUMENT

(75) Inventor: Colin C. O. Goble, Wales (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 09/403,389
(22) PCT Filed: Apr. 24, 1998
(86) PCT No.: PCT/GB98/01202
    § 371 Date: Dec. 20, 1999
    § 102(e) Date: Dec. 20, 1999
(87) PCT Pub. No.: WO98/47436
    PCT Pub. Date: Oct. 29, 1998

(30) Foreign Application Priority Data

Apr. 24, 1997 (GB) .................................................. 9708268

(51) Int. Cl.⁷ .................................................. A61B 18/18
(52) U.S. Cl. ................................ 606/41; 606/34; 606/35; 606/38
(58) Field of Search ................................ 606/32, 34, 33, 606/35, 38, 41, 42

(56) References Cited

U.S. PATENT DOCUMENTS

| 3,566,877 | 3/1971 | Smith et al. . |
| 3,913,583 | 10/1975 | Bross . |
| 4,154,246 | 5/1979 | LeVeen . |
| 4,237,898 | 12/1980 | Whalley . |
| 4,356,458 | 10/1982 | Armitage . |
| 4,373,581 | 2/1983 | Tollener . |
| 4,375,051 | 2/1983 | Theall . |
| 4,551,690 | 11/1985 | Quist . |
| 4,621,242 | 11/1986 | Theall, Jr. et al. . |
| 4,629,940 | 12/1986 | Gagne et al. . |
| 4,674,481 | 6/1987 | Boddie, Jr. et al. . |
| 4,679,007 | 7/1987 | Reese et al. . |
| 4,799,480 * | 1/1989 | Abraham et al. ................. 607/152 |
| 4,945,912 | 8/1990 | Langberg . |
| 4,951,009 | 8/1990 | Collins . |
| 5,001,649 | 3/1991 | Lo et al. . |
| 5,019,076 | 5/1991 | Yamanashi et al. . |
| 5,065,118 | 11/1991 | Collins et al. . |
| 5,187,454 | 2/1993 | Collins et al. . |
| 5,195,045 | 3/1993 | Keane et al. . |
| 5,246,438 | 9/1993 | Langberg . |
| 5,300,068 | 4/1994 | Rosar et al. . |
| 5,364,392 | 11/1994 | Warner et al. . |
| 5,370,644 | 12/1994 | Langberg . |
| 5,392,018 | 2/1995 | Collins et al. . |
| 5,405,346 | 4/1995 | Grundy et al. . |
| 6,074,386 * | 6/2000 | Goble et al. ........................ 606/34 |
| 6,203,516 * | 3/2001 | Kepley ................................ 606/38 |

FOREIGN PATENT DOCUMENTS

| 351 2957 | 10/1986 | (DE) . |
| 122 403 A1 | 10/1984 | (EP) . |
| 0 694 290 A2 | 1/1996 | (EP) . |
| 714 106 A1 | 5/1996 | (EP) . |

(List continued on next page.)

Primary Examiner—Linda C. M. Dvorak
Assistant Examiner—David M. Ruddy
(74) Attorney, Agent, or Firm—Nixon & Vanderhye, P.C.

(57) ABSTRACT

In an electrosurgical instrument susceptible to varying load impedance, particularly varying load reactance, a fixed frequency radio frequency generator has an output stage (Q1, Q2, TR2–TR4, C1, VC2, 42) consisting of at least one output power device and, coupled to the power device, an output network with a load-dependent resonant condition. To compensate for variations in the load reactance, the output network has a dynamically variable capacitor (VC2) which maintains the tuning of the network substantially constant. Variation of the capacitor (VC2) is performed by means of a phase comparator and servo device (44) which are responsive to variations in phase difference occurring in the output stage due to load reactance changes.

25 Claims, 4 Drawing Sheets

FOREIGN PATENT DOCUMENTS

| | | |
|---|---|---|
| 270 819 A2 | 6/1998 | (EP). |
| WO 93/15850 | 8/1993 | (WO). |
| WO/95/34945 | 12/1995 | (WO). |
| WO 96 39085 A | 12/1996 | (WO). |
| WO 97 15237 A | 5/1997 | (WO). |

* cited by examiner

ELECTROSURGICAL INSTRUMENT

BACKGROUND OF THE INVENTION

This invention relates to a radio frequency generator for use with a variable impedance load, and in particular to an electrosurgical instrument having a monopolar electrode unit incorporating such a generator, the operating frequency of the generator being typically in excess of 5 MHz.

A known electrosurgical system comprises a handpiece, a monopolar electrode unit having a single treatment electrode projecting from the handpiece, a generator unit, and a cable coupling the generator unit to the handpiece. Such systems are commonly used for various types of electrosurgery. Normally, a conductive pad is applied to the body of the patient and connected to a return terminal of the generator unit to provide a return path for electrosurgical currents. Disadvantages of this arrangement include the localisation of electrosurgical currents in tissue in the region of the return pad and, particularly at higher frequencies, the unpredictability of reactive components created by the cable between the generator and the handpiece, leading to unpredictable voltage levels at the electrode.

These disadvantages are overcome at least in part by an instrument described in the applicant's International Application No. PCT/GB96/02577 which discloses an electrosurgical instrument comprising a handpiece, a monopolar electrode unit having a single treatment electrode projecting from the handpiece, and a radio-frequency generator within the handpiece, the generator having a single direct radio-frequency output connection, which output connection is coupled to the electrode. The generator is otherwise isolated from external elements. In particular, the generator has no other direct radio frequency output connection to, for example, an earthed element or to a return pad. By providing the generator within the handpiece, unpredictable impedance changes due to the effects of supplying radio-frequency currents through a cable are avoided. Radio-frequency return currents pass between the patient and the generator by stray capacitive coupling via a conductive shield located around the generator.

Preferably, the operating frequency of the generator is 5 MHz or greater. The higher the frequency, the greater the attainable current level due to the reduced reactance of the return path at raised frequencies. The generator may be powered from a battery within the handpiece. This minimises radiated interference.

The presence of an electrically conductive shield around the generator minimises the variation in stray capacitance caused by the user gripping the handpiece in different ways. The shield is preferably isolated from the generator and may form a tubular handpiece body, e.g. in the form of a metallic casing, or the handpiece body may be formed of an electrically insulative material which is metallised to provide the conductive shield. Where the metallisation layer is on the outside of the handpiece body, or the handpiece body is itself metallic, the outer metallic surface is preferably covered by an electrically insulating outer layer. Provision of the shield reduces stray capacitance variations because the capacitance between the relevant generator conductors and the shield is constant, and the shield provides a conductive body of constant area capacitively coupled to the patient.

Although the shield reduces variations in stray capacitance, the variable impedance load which results from this and from the inevitable variations in load caused by changing conditions at the tissue-to-electrode interface poses considerable difficulties in maintaining energy efficiency. To a lesser degree, also it poses difficulties in preventing output device breakdown due to transient mismatches.

BRIEF SUMMARY OF THE INVENTION

With these difficulties in mind, according to a first aspect of the present invention there is provided a radio frequency (r.f.) generator capable of operating at a substantially fixed frequency under varying load conditions, the generator having an output stage comprising an output power device and, coupled to the power device, an output network including a treatment electrode output node, wherein the output network has a load-dependent resonant condition and includes a variable reactance element arranged to compensate at least partially for output network mistuning effects due to variations in load impedance. According to another aspect, the invention provides a r.f. generator capable of operating at a substantially fixed frequency under varying load conditions, the output stage of the generator including a resonant output circuit which has a variable reactance element such as a variable capacitor arranged to compensate, at least partially, for changes in load impedance. The capacitor is automatically varied in response to sensed load impedance changes by, for instance, monitoring phase changes in the output stage and driving the capacitor, preferably mechanically, such that its capacitance is altered in a manner which brings a sensed phase difference to a preferred value or to within a preferred range. Preferably the variable capacitor is coupled across the secondary winding of an output transformer of the generator (which may be an isolating transformer or an auto-transformer), forming part of a parallel tuned output circuit, the tuning of which is affected by the impedance of the load.

In this way, a change in load reactance can be compensated for so as to maintain tuning of the output resonant circuit as far as practicable thereby to present the output device or devices (typically a pair of power transistor switching devices such as power MOSFETs) with an at least approximately real load impedance. It will be appreciated, then, that variations in generator load impedance can be accommodated within a wide range without altering the frequency of operation.

This auto-tuning effect allows the use of a high-Q output stage for efficient coupling of the generator output, a requirement that is important in the case of a self-contained battery-powered handheld electrosurgical instrument as described above in which efficient operation is assisted by good coupling between the instrument, the user and the patient.

Phase information, representing load reactance, for controlling the variable capacitor may be obtained by comparing output phase with the phase of a driving signal. e.g. the r.f. signal supplied to the primary of an output transformer or a driving signal applied to the base or gate connection of an output device. The phase difference signal obtained is then amplified to provide a capacitor drive signal of a polarity such that as load impedance decreases, the variable capacitance also decreases and such that, in the case of the variable capacitor being connected across the output impedance (e.g. the transformer secondary winding), a greater proportion of the available current is supplied to the load.

It should be noted that the output circuit of the generator may also include an output coupling capacitor (i.e. in series in the generator output line) and that the variable capacitor may constitute that coupling capacitor since it also forms part of the output resonant circuit. In that case a decreasing load impedance, while being used to decrease the variable capacitance value, also decreases the available output current. This coupling capacitor variation can be used to limit the load on the generator output device or devices.

The variable capacitor itself may comprise parallel capacitor plates, and means for varying the spacing between the plates such as a piezo-electric actuator. Such a device has the advantage of being able to withstand the high voltages associated with electrosurgical treatment and to operate quickly, typically within 10 ms. Much faster response times are possible depending on the nature of the piezo-electric actuator used. Generally, a high dielectric constant layer is interposed between the capacitor plates.

The invention includes an electrosurgical instrument incorporating a generator as set out above within a handpiece. The instrument has a monopolar treatment electrode projecting from the handpiece, and the variable reactance element of the generator is preferably located at or adjacent the entry location of the electrode into the handpiece.

BRIEF DESCRIPTION OF THE DRAWINGS

The invention will now be described by way of example with reference to the drawings in which.

DETAILED DESCRIPTION OF THE PREFERRED EMBODIMENT

Figure 1:
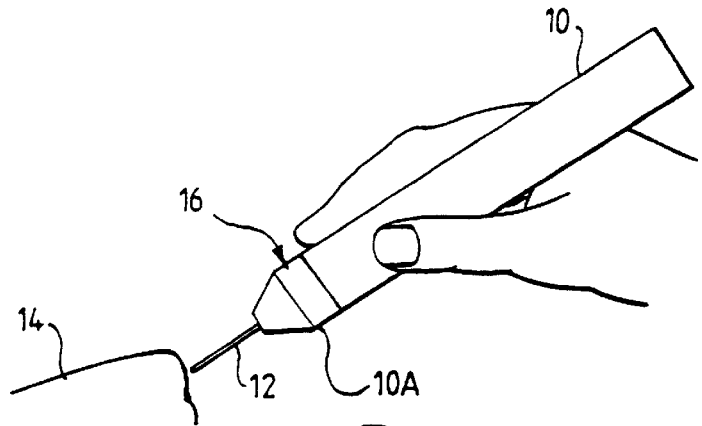
FIG. 1 is a diagram of an electrosurgical instrument, shown in use.

Referring to FIG. 1, a self-contained electrosurgical instrument comprises an elongate cylindrical handpiece 10 which may be held "pencil-fashion" as shown. One end portion 10A of the handpiece is tapered and an electrode unit in the form of a single treatment electrode 12 projects axially from that end so that it may be brought into contact with the body 14 of a patient. An activating switch 16 is provided on the tapered end portion 10A. The body 10 of the handpiece may be formed from sheet metal, and provided with an insulating covering made from, for instance, a film material. Alternatively, the handpiece body 10 may be moulded from an electrically insulative plastics material, and metallised either on the inner or the outer surface. If the metallisation is on the outer surface, an electrically insulating coating is provided to isolate the metallisation from the user's hand.

Figure 2:
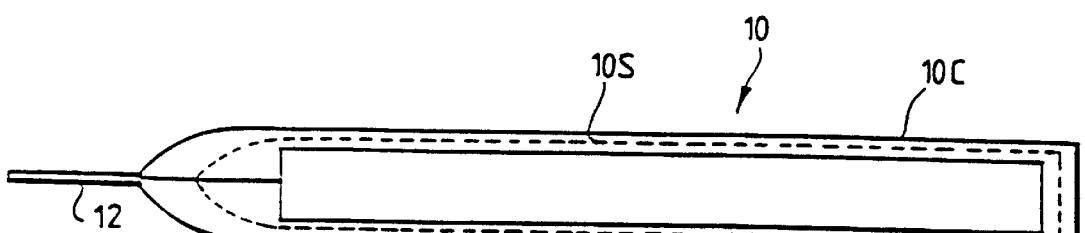
FIG. 2 is a diagrammatic longitudinal cross-section of the instrument.

In the diagrammatic cross-section of FIG. 2, the handpiece body 10 is shown as comprising the conductive shield 10S and an insulation case 10C. An internal electronic unit 18 comprising a radio frequency generator and a battery is contained within the shield 10S. Although it is not essential for the electronic unit 18 to be completely encased by the shield 10S as shown, it is preferable that at least the generator part lies with the lengthwise extent of the shield. The shield 10S has a number of useful properties. The internal electronic unit 18 has a non-uniform mass and distribution within the case, with different potentials relative to earth. The shield 10S provides a uniform surface of the same or uniform potential. By making the insulation layer 10I a minimum size and thickness, the size of the shield can be made a maximum and capacitive coupling both to the patient, the user and external earthed objects can be made a maximum.

By making shield circumferentially continuous, the internal electronics are also effectively screened against the potentially interfering levels of RF radiation. Making the case out of metal to provide the shield provides uniform heat distribution and therefore improves the dissipation of power generated within the electronic unit due to inefficiencies.

Figure 3:
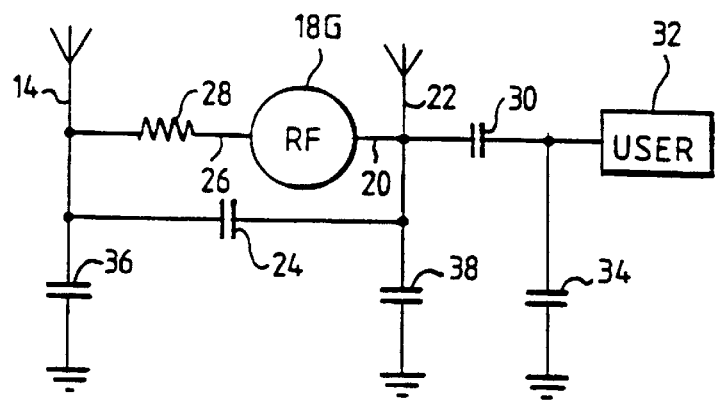
FIG. 3 is an equivalent electrical circuit diagram of the instrument when in use.

Referring to FIG. 3, the equivalent circuit of the instrument when in use is now considered. Inside the handpiece body, there is provided a radio frequency (RF) generator 18G operable at a frequency within one of the industrial, scientific or medical bands above 5 MHz (switch 16 and shield 10S are not shown in FIG. 3). In the preferred instrument, the operating frequency is 40.65 MHz. Other possible frequencies include 6.79 MHz, 13.65 MHz, 27.1 MHz and 915 MHz. The generator has an output connection coupled to the electrode 12 (FIG. 1), and has no other output connection for direct conduction of current to the patient. Conductive elements of the generator 18G (the elements are shown figuratively by the reference 20 in FIG. 3) act as an antenna 22 and are capacitively coupled, indirectly via the conductive shield 10S of the handpiece body 10 (see FIGS. 1 and 2) via capacitance 24 to the patient 14, represented as a second antenna in FIG. 3. The electrode to tissue interface is represented by line 26. Thus, when in use, the active output connection of the generator 18G is connected to the patient 14 through the tissue being operated on, the resistance of this tissue being represented by resistance 28 in FIG. 3. The value of this resistance is typically 1 k$\Omega$, and can drop to as low as 100$\Omega$.

The radiating conductors 20 of the generator 18G are also capacitively connected to the user by capacitance 30, which is the series combination of the generator-to-shield and shield-to-user capacitances, the user 32 being, in turn capacitively coupled to ground as represented by capacitor 34. Since the patient 14 is also capacitively coupled to ground (as represented by capacitor 36 in FIG. 3), there exists an indirect as well as a direct capacitive path between the user 32 and the patient 14. Similarly, there is an indirect path from generator conductive elements 20 through the capacitance 38 of the handpiece body 10 (specifically the shield 10S) to ground and the series capacitance 36 between the patient 14 and ground. The total capacitance between the generator 18G and the patient 14 resulting from the direct generator-to-patient capacitance 24, handpiece-body-to-user capacitance 30, user-to-ground, body-to-ground, and patient-to-ground capacitances 34, 38 and 36 respectively, is at least 15 pF.

Not shown in the drawings is a battery which is also housed within the handpiece body 10. This is preferably a nickel-cadmium or lithium-ion battery, rechargeable via terminals in the opposite end of the body 10 from the electrode 12.

This instrument is primarily, but not exclusively, intended for fine surgical work, such as spinal, neurological, plastic, ear-nose-and-throat and dental surgery, and office procedures.

Figure 4:
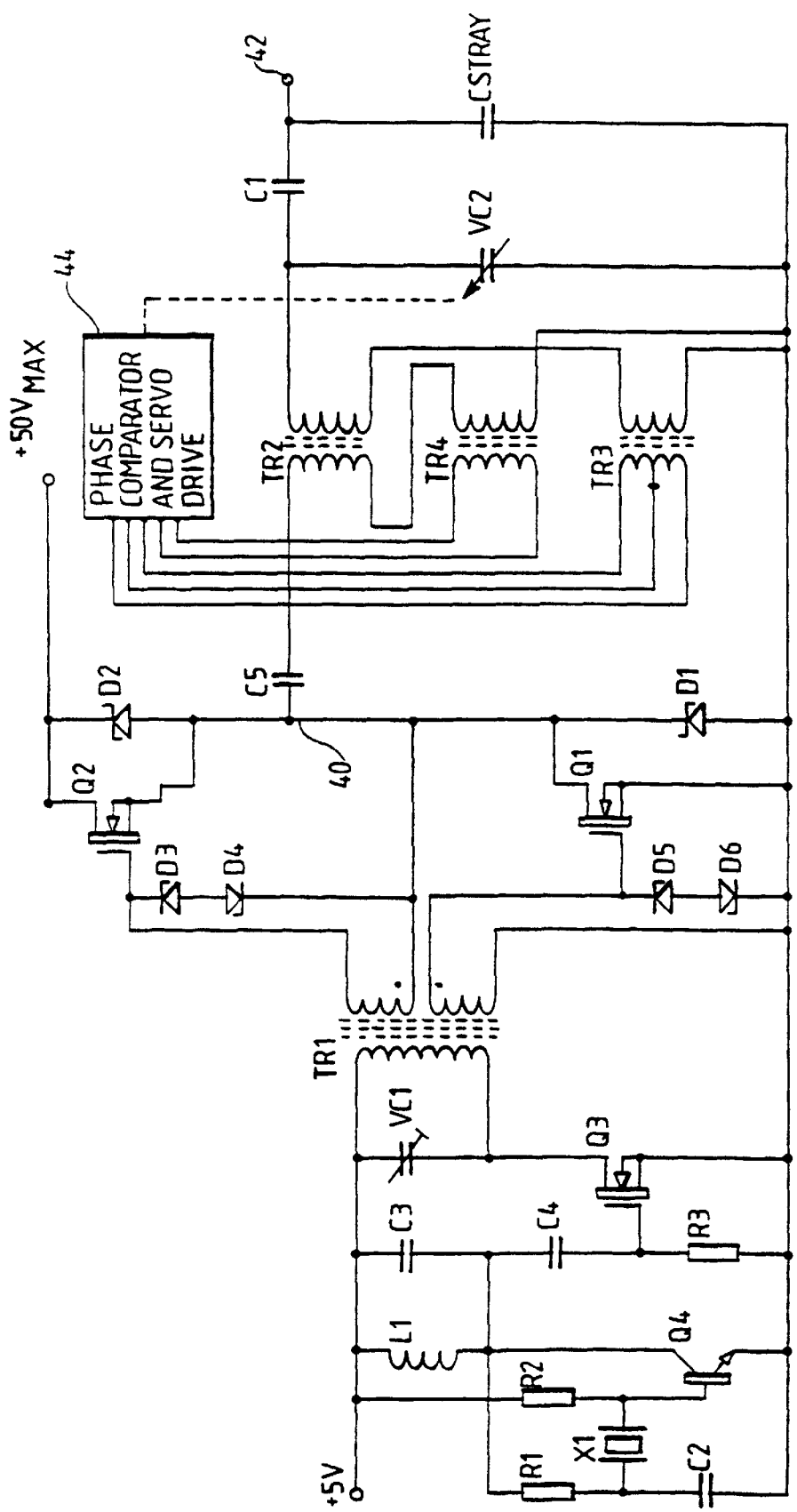
FIG. 4 is a simplified circuit diagram of a generator in accordance with the invention and forming part of the instrument of FIGS. 1 and 2.

Referring now to FIG. 4 of the drawings, a generator for the instrument comprises a fixed frequency crystal oscillator based on transistor Q4, feeding a driver stage based on transistor Q3 and having a driver transformer TR1, and a push-pull output stage based on transistors Q1 and Q2.

Transistors Q1, Q2 are MOSFET devices coupled between a high voltage supply (typically 50 volts) and having a common output connection 40 from which a radio frequency power signal at the frequency of the oscillator is fed via coupling capacitor C5 to the primary winding of an output transformer TR2. The secondary winding of the transformer TR2 is coupled to the generator output 42 via a coupling capacitor C1. Variable capacitor VC2 acts as a tuning element, in conjunction with the capacitance $C_{stray}$ which represents the stray capacitance to ground of the electrode and conductors connected to it. Coupled in series with the primary and secondary windings of transformer TR2 respectively are sensing transformers TR3 and TR4, the secondary windings of which feed a phase comparator and servo drive circuit 44 for driving the variable capacitor VC2.

It will be seen that the output stage has two resonant circuits. A series circuit comprising capacitor C5, the leakage inductance of transformer TR2, and TR3, and a series circuit comprising the secondary winding of transformer TR2 (the main element), the primary winding of TR4 (only signal level), in conjunction with the capacitor array formed by variable capacitor VC2, coupling capacitor C1 and the stray capacitance $C_{stray}$. The phase relationship between these two resonant circuits varies with both load and stray capacitance. The series resonant circuit is comparatively unaffected, but the parallel circuit, connected to the output 42, is affected by both load and stray capacitance. Accordingly, by deriving sensing signals, using transformers TR3 and TR4, from the output circuit (associated with output 42) and a portion of the circuit upstream of the output circuit, in this case the circuit associated with the primary winding of the output transformer TR2, it is possible to derive a phase difference signal which can be used to alter the capacitance of capacitor VC2 and thereby compensate for the detuning variations in load and stray capacitance.

At this point it should be mentioned that any fixed value impedance matching circuit necessarily appears either inductive or capacitive to the output switching devices Q1, Q2, which impairs the switching efficiency. Since, however, such impedance changes are accompanied by phase changes, an output stage employing a resonant tank circuit to minimise harmonics can be used to derive the phase sensing signals for the phase comparator 44.

Figure 5:
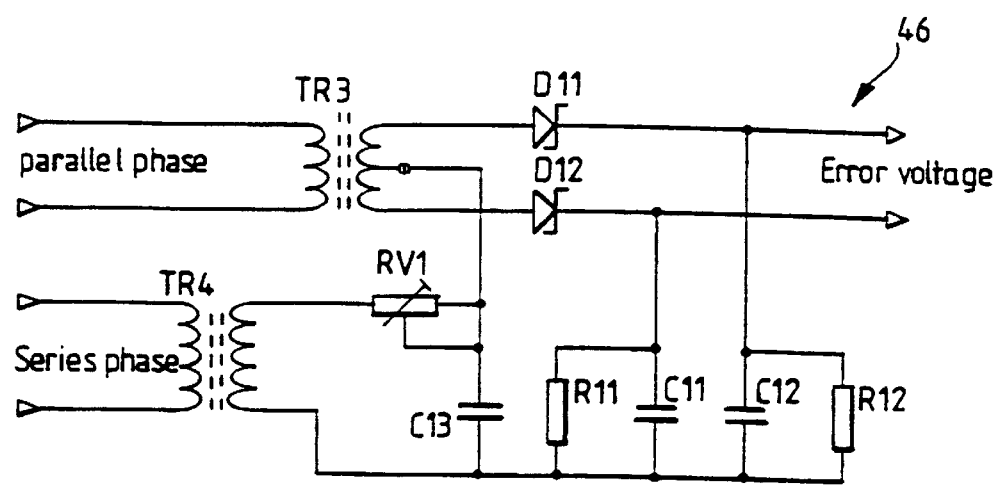
FIG. 5 is a circuit diagram of a phase comparator.

The phase comparator is illustrated in more detail in FIG. 5, together with transformers TR3 and TR4. Signal levels for the phase comparator 44 are provided by the secondary windings of transformers TR3 and TR4 as described above. These provide the phase information from each of the tuned circuits associated with the transformer TR2. By using a split winding for the transformer receiving the parallel phase signal, independent halfwave rectification of alternate cycles occurs by virtue of diodes D11, D12. By mixing both phases of the series phase signal, the phase comparator is corrected. The error voltage developed at the output of the halfwave rectifier D11, D12 only reaches a null, however, when the two sensing signals have a phase relationship offset by 90° with respect to each other. A preset phase shift is provided by the combination of variable resistance RV1 and capacitor C13 connected across the secondary winding of transformer TR4, as shown in FIG. 5, to set the preferred phase difference between the primary and secondary sides of the output transformer TR2 (FIG. 4). Smoothing of the rectifier output voltages is provided by the resistor-capacitor combinations R11, C11 and R12, C12 in FIG. 5, and the output error voltage derived from output 46 is amplified by a comparator (not shown) and passed to a suitable driver circuit (also not shown). This driver circuit incorporates a dominant pole to compensate for potential instability in the feedback loop due to, for example, mechanical resonance in the assembly associated with the variable capacitor VC2.

Referring back to FIG. 4, the variable capacitor VC2, coupling capacitor C1, and stray capacitance $C_{stray}$ of the output capacitor arrangement all have an effect on the tuning of the output resonant circuit. By using the variable capacitor element as the tank capacitor, maximum current delivery can be obtained. In particular, the comparator and driver are arranged such that as the load impedance decreases and a corresponding change in phase difference occurs accross the output transformer TR2, the capacitance of variable capacitor VC2 decreases, and a greater proportion of the available current is supplied to the load. It should be noted that the variable capacitance can, as an alternative, be used instead as the output coupling capacitor (C1). In this instance, decreasing load impedance decreases both the variable coupling capacitance and the available current, which is useful in instances where the r.f. switching devices Q1, Q2 need to be protected against heavy loading.

The variable capacitor VC2 may take different forms. It is preferred that it is constructed as a parallel plate capacitor, the separation of the plates being controlled by a piezo-ceramic actuator. The actuator can be manufactured in two distinct forms: (a) a bending strip which acts in a manner similar to a bimetallic strip or (b) a longitudinal solid piezo-electric element (which may be single or multi layered). Actuators of this kind are available from Morgan Matroc, Inc. of Bedford, Ohio, USA.

The bending strip type of actuator produces mechanical movement in response to a changing applied voltage by creating differential expansion between two bonded materials. The bend can be performed by piezo-ceramic material bonded to a metal substrate. Since ceramic can be poled for compression for as well as for expansion, movement can be brought about in both directions. It is also possible to coat both sides of a metal substrate with piezo-material so that each coating is poled in the opposite direction to enhance the degree of movement. When a voltage is applied to the strip, bending occurs. The applied voltage is typically between 50 and 100 volts to produce adequate movement for varying the capacitance of the variable capacitor. Typically, a capacitance change of 8 to 24 pF is achievable.

With the longitudinal piezo-electric actuator, the piezo movement is used directly. The actuator is made up of a sandwich of devices to achieve sufficient movement in response to applied voltages. In general, the longitudinal piezo actuator has a more rapid response time than the bending strip variety.

It is also possible to alter the capacitance of variable capacitor VC2 by an electromechanical or electromagnetic technique, such as using a moving coil device.

The capacitor itself (not shown in the drawings) comprises parallel plates with a thin intervening dielectric layer having a high dielectric constant. The preferred material is mica, which is available in thin laminate form. Such material has a dielectric strength of between 40 to 200 kV per mm. Since the capacitor is used as a tank circuit tuning capacitor or power coupling capacitor, as described above, voltages across the capacitor plates can reach 1 kV. Typically, the thickness of the dielectric layer is in the region of 25 $\mu$m to 50 $\mu$m. With a relative dielectric constant of 6, it is possible to construct a parallel plate capacitor with a capacitance of 2 pF per mmsq. With a total deflection of 50 $\mu$m, the minimum capacitance is, therefore, 0.16 pF/mmsq.

With regard to the physical position of the variable capacitor VC2 within the handpiece shown in FIGS. 1 and 2, it is advantageous to mount it in the region of the entry of the electrode 2 into the handpiece in order to minimise the lead length between the output 42 (FIG. 4) of the generator and the exposed electrode 12.

While the speed of response of the variable capacitor VC2 and its associated control circuitry is rapid, the nature of electrosurgical action is such that some transient mismatch will still occur due to very rapid changes in load impedance (for example due to arc formation and collapse). To minimise the effect of voltage transients on the output devices Q1, Q2, reversed biased Schottky diodes D1, D2 are provided on each of the output MOSFETs Q1, Q2, as shown. Excess voltage across devices Q1, Q2 at high rates of change is limited not so much by the conduction of the diodes D1, D2, but rather by their varactor behaviour. Although these diodes D1, D2 increase switching capacitance, this can be compensated for by driving the output stage as a partially inductive load so that the net effect on the output devices is purely resistive except when extreme mismatches occur.

Figure 6:
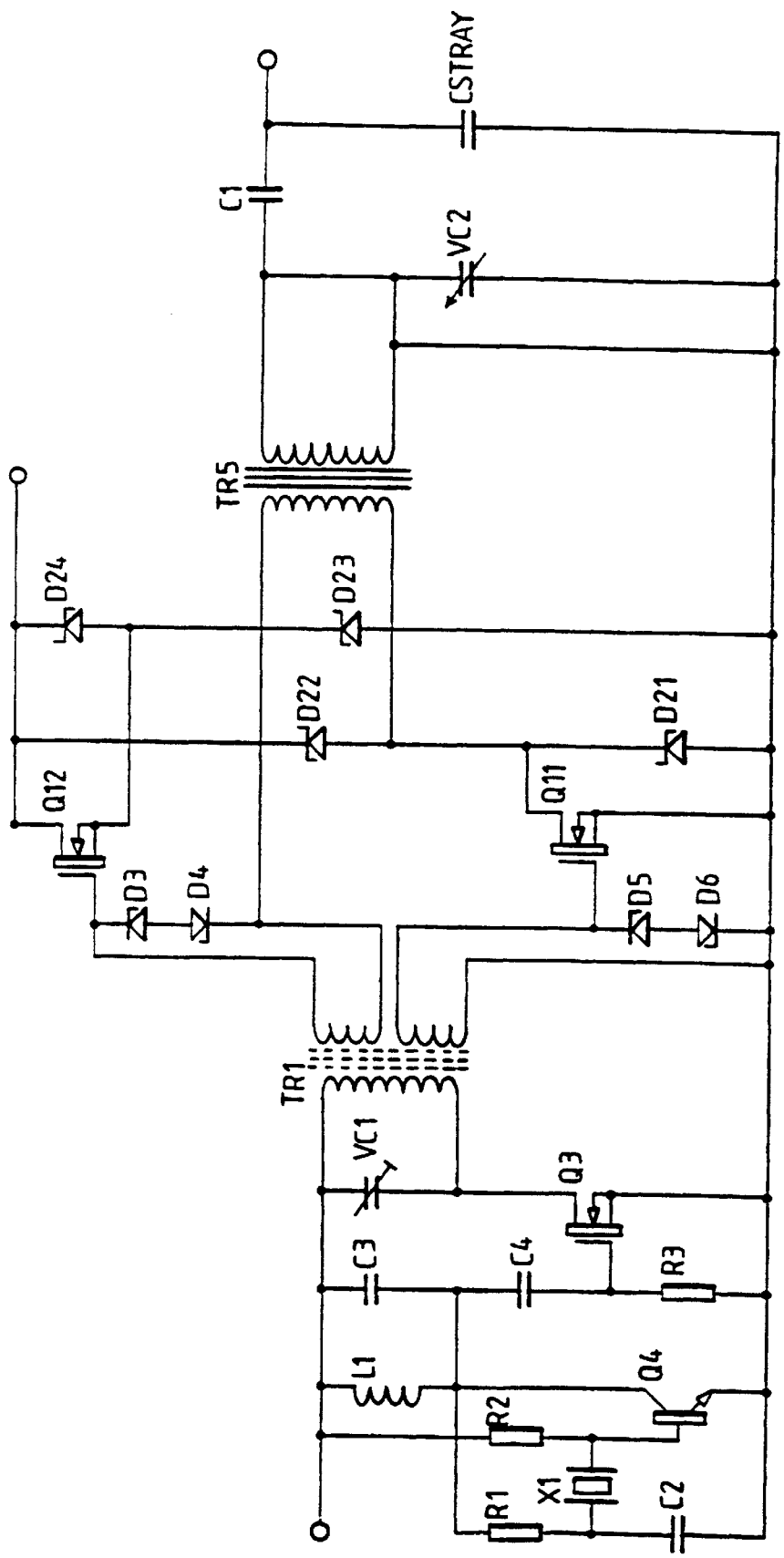
FIG. 6 is a simplified circuit diagram of an alternative generator in accordance with the invention.

The output stage of the generator shown in FIG. 4 is a class C output stage of totem pole configuration connected rail-to-rail. An alternative output stage is shown in FIG. 6. In this case, the crystal oscillator and driver based on transistors Q4 and Q3 respectively remain the same as do the clamping zener diodes D3 to D6 connected across the gate connections of the output devices Q11, Q12. However, the output devices Q11, Q12 are arranged in a half-bridge configuration with additional Schottky diodes, as shown in FIG. 6, and with the output devices having the primary winding of the output transformer TR5 coupled in series between them. The output resonant circuit remains the same as in the embodiment of FIG. 4.

For simplicity, the phase sensing circuits are not shown in FIG. 6. However, it should be noted that the phase comparator of FIG. 5 may be used, with one input transformer coupled in the r.f. gate drive circuits for the output devices Q11, Q12 and the other coupled, as before, in series with the secondary winding of the output transformer TR1.

In summary, the circuitry described above provides extremely fast capacitance change by use of a rapidly responding linear actuator operating over a small range of movement, and phase comparison by means of a variable reactance element in the output resonant circuit. A drive for the variable reactance element is provided in response to phase comparison.

What is claimed is:

1. An electrosurgical instrument comprising:
   a handpiece,
   a single treatment electrode projecting from the handpiece, and
   a generator capable of operating at a substantially fixed frequency under varying load conditions, the generator having an output stage comprising:
      an output power device, and, coupled to the power device,
      an output network including a treatment electrode output node,
      wherein the output network has a load-dependent resonant condition and includes a variable reactance element arranged to compensate at least partially for output network mistuning effects due to variations in load impedance,
      the generator treatment electrode output node being connected to the treatment electrode,
   the instrument being, arranged such that the generator radio frequency return path during use occurs by electromagnetic field transmission through air between the patient and the instrument.

2. A generator according to claim 1, wherein the variable reactance element is associated with a signal path between the power device and the said node.

3. A generator according to claim 1, including a sensing circuit having an output coupled to the variable reactance element, wherein the sensing circuit is arranged to sense changes in load impedance and to produce a load impedance responsive adjustment signal at the said output, and wherein the reactance element is arranged such that its reactance is adjustable in response to the adjustment signal thereby to perform the said compensation.

4. A generator according to claim 3, wherein the sensing circuit is arranged to sense changes in load reactance.

5. A generator according to claim 3, wherein the sensing circuit comprises a phase comparator having inputs coupled to different respective parts of the output stage and arranged to generate at the sensing circuit output an adjustment signal which causes the reactance element to be adjusted so as to bring the phase difference between signals at the phase comparator inputs to a predetermined value or to within a predetermined range.

6. A generator according to claim 1, wherein the variable reactance element is a variable capacitor.

7. A generator according to claim 1, wherein the variable reactance element includes a servo device.

8. A generator according to claim 1, wherein the output stage includes an output transformer and the variable reactance element is coupled to a secondary winding of the transformer.

9. A generator according to claim 1, wherein the variable reactance element forms part of a parallel-tuned output network.

10. A generator according to claim 9, wherein the variable reactance element is a capacitor and the tuned circuit includes a transformer winding.

11. A generator according to claim 1, wherein the output network includes a generator output line, and wherein the variable reactance element is connected in series in the output line.

12. A generator according to claim 11, wherein the variable reactance element is a capacitor.

13. A generator according to claim 1, wherein the variable reactance element forms part of an output circuit between the power device and an output node of the generator.

14. A generator according to claim 1, wherein the generator has a conductive element acting as an antenna.

15. A generator according to claim 1, having an operating frequency in excess of 5 MHz.

16. An instrument according to claim 1, including a conductive body arranged to provide stray capacitance coupling to the patient during use of the instrument as a return path for radio frequency currents.

17. An instrument according to claim 1, having only a single direct radio frequency output connection, the return path being provided in use by a conductive body capacitively coupled to the patient by stray capacitance.

18. An instrument according to claim 1, operable at a frequency in excess of 5 MHz.

19. An instrument according to claim 6, wherein the variable capacitor is a parallel plate capacitor, the separation of the plates being controlled by a piezo-ceramic actuator.

20. An instrument according to claim 19, wherein the piezo-ceramic actuator is a bending strip which acts in a manner similar to a bimetallic strip.

21. An instrument according to claim 19, wherein the piezo-ceramic actuator is a longitudinal solid piezo-electric element.

22. An instrument according to claim 21, wherein the piezo-electric element is single.

23. An instrument according to claim 21, wherein the piezo-electric element is multi-layered.

24. An instrument according to claim 1, wherein the variable reactance element is a parallel plate capacitor wherein the plates are separated by a piezo ceramic actuator that is a bending strip.

25. An instrument according to claim 1, wherein the variable reactance element is a parallel plate capacitor wherein the plates are separated by a piezo ceramic actuator that is a longitudinal solid piezo electric element.

* * * * *